United States Patent [19]
Kross

[11] Patent Number: 5,667,817
[45] Date of Patent: Sep. 16, 1997

[54] METHOD AND COMPOSITION FOR PREVENTION AND TREATMENT OF FEMALE LOWER GENITAL TRACT MICROBIAL INFECTIONS

[75] Inventor: Robert D. Kross, Bellmore, N.Y.

[73] Assignee: Alcide Corporation, Redmond, Wash.

[21] Appl. No.: 703,942

[22] Filed: Aug. 28, 1996

Related U.S. Application Data

[63] Continuation of Ser. No. 133,465, Oct. 8, 1993, abandoned, which is a continuation-in-part of Ser. No. 854,286, Mar. 20, 1992, Pat. No. 5,252,343.

[51] Int. Cl.$^6$ .......................... A61K 33/00; A61K 33/20
[52] U.S. Cl. .......................... 424/661; 424/662; 424/663; 424/664; 424/665; 514/931; 514/932; 514/933; 514/934; 514/967; 514/968
[58] Field of Search .......................... 424/661, 662, 424/663, 664, 665; 514/931, 932, 933, 934, 967, 968

[56] References Cited

U.S. PATENT DOCUMENTS

| | | | |
|---|---|---|---|
| 4,692,262 | 9/1987 | Brown et al. | 252/106 |
| 4,956,184 | 9/1990 | Kross | 424/661 |
| 4,986,990 | 1/1991 | Davidson et al. | 424/665 |
| 5,019,402 | 5/1991 | Kross et al. | 424/665 |
| 5,100,652 | 3/1992 | Kross et al. | 424/53 |
| 5,252,343 | 10/1993 | Kross | 424/661 |
| 5,489,435 | 2/1996 | Ratcliff | 424/422 |

OTHER PUBLICATIONS

Abdel–Rahman et al., "Subchronic Vaginal toxicity studies of Alcide Allay® Gel and liquid in guinea Pigs," Drug and Chemical Toxicology, vol. 10 (Mar. 4), 1987, pp. 257–274.

Colben et al., "Development of a Model to Study Endometritis in Mares," *Journal of Equine Veterinary Science* 7(2); 73–76, 1987.

Jones, L. Meyer (ed.), *Veterinary Pharmacology and Therapeutics*, 3$^{rd}$ Ed., Iowa State University Press, Ames, Iowa, USA, 1965, p. 577.

Jubb, K.V.F., et al. (eds.), *Pathology of Domestic Animals*, 3$^{rd}$ Ed., vol. 3, Academic Press, Inc., Orlando, Florida, 1985, pp. 330–332.

Harakeh, S., et al., "Inactivation of bacteria by Purogene," *Journal of Applied Bacteriology*, 64:459–463, 1988.

Wyngaarden, J.B. et al. (eds.), *Cecil Textbook of Medicine*, 18$^{th}$ Ed., W. B. Saunders Company, Philadelphia, PA, 1988, pp. 1704–1706.

*Primary Examiner*—John Pak
*Attorney, Agent, or Firm*—Seed and Berry LLP

[57] ABSTRACT

Methods for preventing and treating microbial infections in the mammalian female lower genital tract such as vulvitis, vaginitis, cervicitis, and endometritis involve the intravaginal and/or intra-uterine infusion of a solution containing a pharmacologically acceptable carrier and chlorine dioxide in an amount ranging from about 5 ppm to 1000 ppm, and having a chlorine dioxide to chlorite ratio of at least 5:1. Typical solutions exhibit a pH compatible with the lower genital tract, e.g., a pH from about 5 to about 7.5. In many embodiments, chlorine dioxide in the solution is produced by reacting a chlorite with a mineral acid and adjusting the pH, by reacting a chlorite with an organic acid having a pK of about 2.8 to 4.2, or by reacting a chlorite at a pH below about 5.5 with a heat-activated saccharide in the presence of an organic acid having a pK of about 2.8 to about 4.2. Sodium chlorite is employed in preferred embodiments.

20 Claims, No Drawings

METHOD AND COMPOSITION FOR PREVENTION AND TREATMENT OF FEMALE LOWER GENITAL TRACT MICROBIAL INFECTIONS

CROSS-REFERENCE TO RELATED APPLICATION

This application is a continuation of U.S. patent application Ser. No. 08/133,465, filed Oct. 8, 1993, now abandoned, which application was a continuation-in-part of U.S. patent application Ser. No. 07/854,286, filed Mar. 20, 1992, which issued as U.S. Pat. No. 5,252,343 on Oct. 12, 1993.

TECHNICAL FIELD

This invention relates generally to the prevention or treatment of endometritis, vaginitis and related microbial infections of the lower genital tract in female mammals, particularly to postpartum infections.

BACKGROUND OF THE INVENTION

Uterine infections and infections of the cervix, vagina and vulva commonly occur in human beings and domestic animals, especially following birth. Typical infecting organisms of the endometrium (uterine mucosa) and contiguous mucosal surfaces in the lower genital tract include, for example, β-hemolytic streptococci, *Candida albicans*, *Klebsiella pneumoniae*, coliform bacteria including *Escherichia coli*, *Corynebacterium pyogenes* and *C. vaginale*, various Campylobacter or Trichomonas species such as *T. vaginalis*, and the like. Even mild vaginitis is uncomfortable, and even where endometritis is mild, the impact on fertility can be substantial. Fertility depression and aberrations of the estrous cycle are typical symptoms. Acute infections can lead to complications; acute endometritis and metritis, for example, can eventually involve all organ layers and cause abortion, extensive hemorrhage, necrosis, abscesses, peritonitis, toxemia or septicemia, and death.

The normal nonpregnant uterus is endowed with a high degree of resistance to infection, and even in the case of specific genital diseases such as brucellosis, trichomoniasis, and Campylobacter infection, is ordinarily incapable of supporting bacterial growth or the persistence of bacteria for any extended period. Normal antibody production plays a role in this resistance, but, more importantly, bacterial clearance from the endometrium and phagocytic response to bacteria are enhanced by estrogen and suppressed by progesterone (Jubb, K. V. F., et al., *Pathology of Domestic Animals*, 3rd ed., vol. 3, Academic Press, New York, 1985, pages 330–332).

The uterus under the influence of progesterone (which includes the pregnant uterus), on the other hand, is very susceptible to nonspecific bacteria and often becomes infected. Some postpartum metritis is a continuation and exaggeration of a gestational uterine infection, but most puerperal infections of the uterus are analogous to wound infections, with organisms entering via the cervix, sometimes in conjunction with obstetrical manipulations. It has been stated, for example, that probably all mares have uterine infections by streptococci within 1 to 3 days after parturition (ibid.).

Ruptures and/or infections of the vagina and vulva are frequently acquired as parturient injuries. Vaginitis that is sexually transmitted or transmitted by other means is even more common. Vaginitis is generally divided into three types: yeast infection (ordinarily *Candida albicans*), trichomonas (typically *T. vaginalis*), and "nonspecific" vaginitis caused by other organisms. Mixed (polymicrobial) infections may also occur.

The outcome of lower genital tract infection is determined by the number and virulence of invading organisms as well as by the environment within the uterus and birth canal and the health of the female. Infections may be "subclinical," where the infection is not directly evident by palpation or visual gynecological examination, or "clinical," which is diagnosed by the presence of visually detectable alterations in the cervix, organ enlargements and other changes, tenderness and pain, discharges, and sometimes foul odors. The endometrium may be congested and swollen, exhibiting small hemorrhages and a prominent leukocytic infiltration; vaginal and vulvar itching may be troublesome. Elevated levels of white cells in response to the infection is often observed, and milk production in postpartum females can be depressed.

Some milder cases of endometritis recover health and fertility spontaneously. Many acute cases, on the other hand, can lead to complications such as chronic endometritis, uterine abscess, parametritis, and the like, and many animal cases are fatal in spite of therapy. Treatments for infection include infusions of antibiotics into the birth canal and uterus, which can be irritating, or systemic administration of antibiotics. Penicillin is the appropriate drug for most streptococcal infections, but enterococci, *E. coli*, *Bacteroides fragilis*, and other gram-negative bacilli often recovered in puerperal infections are relatively unresponsive to it. As a consequence, a combination of drugs is preferable to penicillin alone, such as streptomycin or kanamycin in combination with penicillin.

Treatment is commonly instituted prior to identification of the specific causative organism or organisms, and antibiotic dosage alterations or drug changes may be necessary after identification of organisms in culture. It is important at the outset to select an antimicrobial which offers the greatest range of efficacy against an array of pathogens that could be causing infection. Use of broad-spectrum antibiotics can, however, lead to tolerance problems and allergies. Antibiotics systemically administered to a nursing mother can contaminate her milk and alter the intestinal flora and have other deleterious effects on the suckling offspring, and, in the case of cow's milk, can render it unfit for consumption or use in processing into cheese or yogurt. Some systemic antibiotic therapies are not recommended for pregnant women, especially during their first trimester. And in veterinary practice, the cost of antibiotics can be prohibitive.

Fungicides are employed to treat yeast infections; for *Candida vaginitis*, intra-vaginal nystatin is typically employed. Unfortunately, antibiotic therapy can increase susceptibility to vaginal candidiasis (*Cecil's Textbook of Medicine*, 18th ed., W.B. Saunders Co., 1988, pages 1704 to 1706), so that treatment of one genital tract infection can exacerbate another. Trichomonad vaginitis is treated with nitroimidazoles, but there is evidence that these are weakly carcinogenic in certain animal systems (ibid.).

It would be desirable to have alternate and adjunct methods for the treatment and prevention of lower genital tract microbial infections in females, such as postpartum infections and vaginitis.

SUMMARY OF THE INVENTION

Briefly stated, the present invention provides a method for treating or preventing microbial infections in the lower genital tract of mammalian females, including both clinical and subclinical endometritis and vaginitis. It also relates to the prophylactic use of compositions that aid in suppressing the bacterial, yeast and trichomonad growth which leads to such infection. The invention further provides a means of countering the inflammatory process which results from microbial infection of the endometrium, vagina and vulva, including various peri-parturient diseases arising from infection and complications relating thereto.

The method involves the intra-uterine or intra-vaginal infusion or douche of an aqueous chlorine dioxide solution comprising from about 0.0005% (5 parts per million, ppm) to about 0.1000% (1000 ppm), and, in some embodiments, more preferably from about 40 ppm to about 600 ppm, of chlorine dioxide, in a pharmaceutically acceptable medium or carrier. One embodiment employs a solution containing about 500 ppm chlorine dioxide. The chlorine dioxide solutions used in the invention have a relative molar ratio of chlorine dioxide to residual chlorite of at least 5:1, typically at least 7.5:1, and preferably at least 10:1.

The chlorine dioxide solution may be provided in a number of ways. For example, it may be formed immediately prior to infusion or douching by combination of a chlorine dioxide liberating compound (such as water-soluble alkali or alkaline earth metal chlorites or mixtures thereof) with a mineral acid such as sulfuric acid, hydrochloric acid, and/or phosphoric acid, followed by adjustment of the pH to about 5 to 7.5. Sodium chlorite is employed in some preferred embodiments.

Alternatively, chlorine dioxide can be formed by reacting a chlorine dioxide liberating compound such as the chlorites mentioned above with an organic acid having a pK of from about 2.8 to about 4.2, such as malic acid, lactic acid, citric acid, mandelic acid, tartaric acid, and mixtures thereof. Chloride ion can optionally be used in these formulations, as can carbohydrate triggering substances that accelerate the formation of chlorine dioxide.

Alternatively, chlorine dioxide can be formed by reacting a chlorine dioxide liberating compound such as the chlorites mentioned above with a saccharide, which has been heat-activated by heating the saccharide to a temperature of from about 50° C. to about 150° C. for at least about 1 minute, typically from about 5 to 240 minutes and preferably from about 20 to 120 minutes, in a solution in the presence of an organic acid having a pK of about 2.8 to about 4.2 and at pH below about 5.5. Typical saccharides used in these formulations include glucose, galactose, mannose, ribose, rhamnose, lactose, sucrose, maltose, and mixtures thereof.

The volume of chlorine dioxide-containing solution used in treatment or prevention according to the method of the invention varies with the size of the mammal and the scope of the infection or potential infection, and can range between about 10 milliliters to about 5 liters.

Pharmaceutically acceptable carriers include any that do not irritate the mammalian lower genital tract, including isotonic solutions containing saline and other inorganic (e.g., phosphates and sulfates) and organic salts. Typical solutions have a pH compatible with the lower female genital tract, e.g., from about 5 to 7.5. The solutions may optionally contain suitable wetting agents and emollients.

DETAILED DESCRIPTION OF THE INVENTION

This invention is based upon the finding that a solution containing chlorine dioxide having defined chlorine dioxide-to-chlorite molar ratios that limit tissue irritation are efficacious in the treatment and prevention of lower genital tract infections in female mammals.

In one embodiment, the present invention is directed to the use of chlorine dioxide for the prevention, mitigation or cure of endometritis, cervicitis, vaginitis, and vulvitis, and/or the alleviation of the associated inflammation, in such a manner as to overcome the rapid loss of antimicrobial activity of the agent which occurs in the presence of significant quantities of organic matter present in lower genital tract infections and in the postpartum birth canal. The invention allows for such treatment without the disadvantage associated with antibiotics employed for such treatment such as gastrointestinal distress, and side effects elicited by the absorption of other drugs.

In contrast to antibiotics, systemic absorption of the compositions of the invention is minimized in treatments using them because of the inorganic nature of chlorine dioxide, and its reductive degradation to chloride as a result of its interaction with organic matter (including bacteria and yeast). It is important to note that materials may be non-inflammatory (i.e., not provoke inflammation) but not anti-inflammatory (i.e., counter the effects of inflammation). Chlorine dioxide has been found to be non-inflammatory, by virtue of being infusible into the birth canal and uterus without evoking the inflammatory response, as well as being anti-inflammatory; see the copending U.S. application Ser. No. 07/930,088, filed Aug. 14, 1992, now abandoned, which is hereby incorporated in its entirety by reference. In order to utilize the germ-killing and non-inflammatory qualities of chlorine dioxide, it is preferable to isolate it from chlorites and its acidic form, chlorous acid (which have detrimental cytotic effects).

To minimize the negative effects caused by chlorite (and chlorous acid in lower pH solutions), techniques are employed which preferably either a) deliver the soluble chlorine dioxide gas in a solution relatively free of harmful chlorite, or b) employ a pre-infusion chemical reaction whereby the chlorite species has substantially converted to chlorine dioxide leaving relatively little chlorite remaining. In both cases, the relative molar ratio of chlorine dioxide to residual chlorite is at least 5:1, typically at least 7.5:1, and preferably at least 10:1. The concentration of chlorine dioxide in the infusate or douche varies from about 5 ppm (mg/liter) to about 1000 ppm, and is typically at least about 10 ppm, preferably above about 20 ppm, and optimally in excess of about 40 ppm. One embodiment employs about 500 ppm. As addressed below, the concentration requirement depends, to a significant degree, on the volume of infusate that is to be employed, since it is the total quantity of chlorine dioxide (i.e., concentration times volume) that is critical to the goal of overcoming the neutralizing effects of organic matter in the birth canal and uterus in order to achieve the antimicrobial effects of the chlorine dioxide.

For the preparation of a chlorine dioxide composition for use in the method of the invention, a chlorine dioxide generating compound is generally reacted with an acid in an aqueous solution. Exemplary chlorine dioxide generating compounds are water-soluble chlorites such as alkali metal chlorites, alkaline earth metal chlorites, and mixtures of these. Sodium chlorite is employed in preferred embodiments.

In conventional means of producing chlorine dioxide solutions, a mineral acid is reacted with a chlorite such as sodium chlorite at such concentrations as to provide rapid evolution of chlorine dioxide. Typical mineral acids include, but are not limited to, sulfuric acid, hydrochloric acid, phosphoric acid, and the like. Such admixture, however, results in a very acidic solution that requires neutralization before use. Typical solutions are neutralized to a pH of from about 5 to about 7.5 prior to use.

Alternatively, a chlorine dioxide generating compound such as the chlorites mentioned above can be reacted with a weaker acid, such as an organic acid having a pK of from about 2.8 to about 4.2. Typical acids include lactic acid, citric acid, malic acid, glycolic acid, mandelic acid, tartaric acid, and mixtures thereof. The preparation of these types of formulations is set out in U.S. Pat. No. 4,986,990 to Davidson and Kross, the disclosure of which is hereby incorporated herein in its entirety by reference. In that patent, concentrations of sodium chlorite and activating acid are both below about 0.01–0.02%, in isotonic saline. Such solutions have been found to be appropriate for use in the uterine infusion treatment of the present invention for chlorine dioxide levels up to about 125 ppm. The solutions may require pH adjustment, e.g., to about 5 to about 7.5. The reactions, upon admixture, are virtually complete within several minutes, and can generate chlorine dioxide solutions in excess of 40 ppm with solution pH's compatible with the birth canal. When higher levels of chlorine dioxide are required, stronger acids and higher levels of chlorite may be used, with subsequent neutralization prior to infusion. Typical solutions can contain up to about 1000 ppm chlorine dioxide.

The inclusion of small amounts of certain activating sugars (e.g., ribose, galactose, mannose) in the formulation, for example, at levels at or below about 1%, can further increase the speed and efficiency of chlorine dioxide formation. It has been found that this reaction, with or without the addition of sugar triggers, can provide the requisite chlorine dioxide-to-chlorite molar ratios of at least 5:1 that are necessary to limit tissue irritation.

The composition may contain chloride ion, which is typically in the form of an alkali or alkaline earth metal salt. For sodium chloride, for example, concentrations can range between about 0.5% to 1.5% by weight; use of other salts requires an appropriate weight percent adjustment. In solutions below pH about 7, chloride ion causes chlorite ion to decompose in an accelerated manner, via the degradation of chlorous acid to form chlorine dioxide. Preferred embodiments of the invention employ solutions that are approximately isotonic to the female lower genital tract.

In another embodiment, chlorine dioxide formation in the reaction between chlorite and weaker acids is catalyzed by heat-activated saccharides. Heat-activated saccharides are prepared by heating saccharides to a temperature of from about 50° C. to about 150° C. for at least about 1 minute, typically from about 5 to 240 minutes. Some heat-activated saccharides are prepared by heating to about 75° C. to about 110° C. for about 20 to 120 minutes. Exemplary saccharides include, but are not limited to, glucose, galactose, mannose, ribose, rhamnose, and disaccharides such as sucrose, lactose, and maltose, and mixtures thereof. Glucose is preferred in one embodiment. Heat-activated saccharides useful in these embodiments of the invention are described in greater detail in U.S. Pat. No. 5,019,402 to Kross and Scheer, the disclosure of which is hereby incorporated herein in its entirety by reference.

The chlorine dioxide solutions are generally buffered mixtures that maintain the douche or infusate at a pH compatible with the lower female genital tract. The pH typically varies between about 4.5 or 5.0 and about 7.5. The solutions can contain other ingredients typical in douches such as, for example, wetting agents (such as nonylphenoxy polyoxyethylene (9)), soothing emollients, and the like. Suitable carriers are chosen for their ability to dissolve or disperse chlorine dioxide as well as provide a composition conducive to infusion. Many such compositions are known in the art, and can include thickening and emulsifying agents and the like, and such carriers are referred to herein as pharmacologically acceptable carriers.

The solutions may be prepared immediately before infusion or douching in one embodiment. In another embodiment, the chlorine dioxide solution may be prepared and stored below a pH of about 5.5. For more particulars about storage, including storage of components and mixing of these prior to use, reference is made to U.S. Pat. Nos. 4,986,990 and 5,019,402, cited above, and references cited therein. Briefly stated, for the delivery of preformed aqueous chlorine dioxide, the following criteria should be met: 1) a storage pH below about 5.5 to minimize the degradation of chlorine dioxide to chlorite and other species; 2) a concentration of sodium chloride or equivalent material sufficient to render the solution approximately isotonic (e.g, from about 0.80 to about 1.0% NaCl); 3) a package container that is virtually impermeable to, and non-reactive with, chlorine dioxide, such as glass and certain grades of polyacrylonitrile and polyvinylidene chloride. Immediately before the douche or infusion, a suitable buffer is typically added to these solutions.

The volume of infusates or douches varies with the size of the animal and the degree of infection or potential infection, and can range between about 10 milliliters to about 5 liters. Example volumes are given hereinafter.

When solutions of the invention are infused into the female lower genital tract, i.e., vagina and uterus, they are well tolerated, producing no noticeable irritation effects in the animals tested. Infusions with solutions of the invention are especially efficacious in the treatment of endometritis in mares, and help raise the fertility rate of infected horses. Infusions also assist in the treatment of bovine post-parturient metritis, and help the discharge of retained placentas.

Another important feature associated with the use of chlorine dioxide infusions for the control of endometritis and related disorders is its fairly rapid reduction to chloride ion, which is a common component of body fluids and tissues in general. This reduction occurs by interaction with organic matter, including bacteria. Topical agents that are non-toxic to vaginal cells without systemic absorption are especially needed for the destruction of potentially resistant isolates and for the treatment of pregnant patients who have recurrent infections.

Since a sufficient excess of the chlorine dioxide provides microbiocidal activity at a more rapid rate than the rate of depletion of the molecule's oxidizing power by the organic environment, some antimicrobial efficacy may be achieved from the chlorine dioxide despite its rapid reduction by organic matter. Thus, a chlorine dioxide infusion into the uterine cavity which may contain significant amounts of organic material (e.g., mucus, serum, and sloughed cells) can still provide antimicrobial activity as shown in Examples hereinafter.

Both reduction of genital tract organic matter with the chlorine dioxide and longer contact time increase the antimicrobial effectiveness of the chlorine dioxide solution. These data suggest that the infusion of a sufficient volume of a chlorine dioxide solution into the vagina and uterus, to overcome residual quantities of materials present postpartum or during infection, could destroy microorganisms present in the environment. In some embodiments illustrated in the Examples hereinafter, volumes of 1 to 4 liters are employed in the treatment of post-parturient Holsteins. Higher chlorine dioxide concentrations in these volumes would similarly enhance the cidal activity. Since residence times of such infusions can be lengthened, there would be ample time for the antimicrobial to operate before being chemically neutralized.

The ability of the chlorine dioxide solutions to bring about a marked reduction in Trichomonas counts in in vitro studies described in greater particularity below as well as to increase fertility in mares having endometritis is significant. Both the cows and horses treated in the Examples exhibited serious conditions, so that the ability of the chlorine dioxide infusion treatment to significantly improve their situations is noteworthy.

Use of the chlorine dioxide solutions of this invention, with their rapid degradation to chloride salts, further allows for their application as a prophylactic treatment for females during periods which predispose them to the development of endometritis, vaginitis and related microbial infections of the lower genital tract, such as after birth. A further application for these solutions is during pregnancy, when ordinary antibiotics are often not administered. The infusion of chlorine dioxide solutions could significantly reduce the impact of microbial invasion of the tract.

EXAMPLES

The following examples are presented to further illustrate and explain the present invention and should not be taken as limiting in any regard.

Example 1

In this Example, Trichomonas vaginalis is killed in vitro using the composition and method of this invention.

A disinfectant solution is prepared by mixing solutions A and B below 1:1 (v/v) immediately prior to use:

| solution A | | solution B | |
|---|---|---|---|
| Lactic Acid | 1.009% | Sodium Chlorite | 0.161% |
| Pluronic F-68 ® | 0.153% | Tetra Na EDTA | 0.045% |
| Sodium Benzoate | 0.040% | USP Purified Water | q.s. |
| USP Purified Water | q.s. | | |

After mixing, the formulation is adjusted to neutrality with phosphate buffer to provide a chlorine dioxide concentration of about 60 ppm.

Ten (10) clinical isolates of Trichomonas vaginalis (TV) are grown in Diamond's media. In test cultures, buffered disinfectant is added to give a 50% concentration and a final concentration of $7.5 \times 10^8$ TV/ml. Upon incubation of the cultures, the disinfectant is cidal at 24, 48, 72, and 96 hours. Control cultures with the same isolates but having no disinfectant show Trichomonas viability at concentrations up to $10^9$ after 24 and 48 hours of incubation.

Comparative cultures incubated with betadine (0.23%, Massengill Medicated Douche®) do not show cidal activity when added to $10^4$ TV/ml cultures and incubated for 24 or 48 hours. On the other hand, Metronidazole® added to the same cultures at levels of 10 µg/ml shows cidal activity when inoculated into cultures containing $10^9$ TV/ml and $10^4$ TV/ml and incubated 24 and 48 hours.

Example 2

This Example shows the efficacy of the composition and of the invention when used as an intrauterine infusion in mares having endometritis. Eight mares that could not conceive because of uterine infections are employed in the study.

A uterine disinfectant solution for use in the study is prepared. An acidic saccharide solution is first prepared by dissolving

| | ingredient | w/w % |
|---|---|---|
| | Dextrose | 9.0 |
| and | 1N NaOH | 3.0 |
| in | Pyrogen-Free Water | 97.55 | and heating to 85° C. with constant stirring on a hot plate. The solution is cooled to room temperature and

| Lactic Acid | 0.45 |
|---|---| is added. The pH is adjusted to 4.5 with dilute NaOH. A chlorine dioxide liberating compound solution is prepared by dissolving

| | $NaClO_2$ | 0.6 |
|---|---|---|
| in | Pyrogen-Free Water | q.s. |

A 1:1 (v/v) mixture of the two solutions yields a disinfectant having a pH of about 5.0.

Uterine infusions of 3–4 oz. of the disinfectant solution yields the following results:

| Case # | Pretreatment Culture | Day[1] | Post-Treatment Culture/ Time of Culture | Bred | Foal |
|---|---|---|---|---|---|
| 1 | β-Strep | −20 | Neg/10 hours | yes | no |
| 2 | β-Strep | −4 | Neg/3 days | yes | yes[2] |
| 3 | Pseudomonas | +1 | Not done | yes | yes |
| 4 | Pseudomonas | −12 | Neg/8 days | yes | no |
| 5 | Pseudomonas | | Pos/3 days β-Strep | no | NA |
| 6 | Pseudomonas | +1 | Not done | yes | yes |
| 7 | Fungal | | Not done Exam: No discharge/ 2 days | no | NA |
| 8 | Pseudomonas | +1 | Not done | yes | yes |

[1]Day of treatment relative to day of breeding
[2]Miscarried

The data show that at least 4 of the 8 mares foaled. Moreover, visual examination show that the treatment eliminated or minimized symptoms of uterine infection.

Example 3

In this Example, the efficacy of the invention in the treatment of bovine post-parturient metritis is evaluated. The clinical response of post-parturient Holstein cows presenting with retained placentas are treated with pH neutral infusions of chlorine dioxide for three days after loss of membranes.

Disinfectant solutions are prepared by adding 5 ml of a 22.5% aqueous Sodium Chlorite to 500 ml of a mixed solution of 0.3N Hydrochloric Acid 0.23% Phosphoric Acid.

The solutions are left standing for 5 minutes, and then 500 ml of a solution containing 2.20% Sodium Hydroxide 1.10% Potassium Phosphate Monobasic ($KH_2PO_4$)

is added. The disinfectant mixture so prepared has a pH of 7.0 and contains 500 ppm $ClO_2$.

Control animals are treated with 1 to 4-liter intra-uterine infusions of sterile phosphate-buffered saline at pH 7.0. (The actual volumes infused depend on the stage of involution of the uterus relevant to the time of foetal membrane loss post-parturition.) Test animals are treated with 1- to 4-liter intrauterine infusions of the above-described disinfectant containing 500 ppm chlorine dioxide. Infusions commence 24 hours after membrane loss. Uterine involution is assessed on days 14, 21, 28, and 35 post-parturition. The infusions are well tolerated, and show no indications of any adverse reactions.

The above description is for the purpose of teaching the person of ordinary skill in the art how to practice the invention, and it is not intended to detail all those obvious modifications and variations of it which will become apparent to the skilled worker upon reading the description. It is intended that all such reasonable modifications and variations be included within the scope of the invention, which is defined by the appended claims. The claims are intended to cover the claimed components and steps in any sequence which is effective to meet the objectives there intended, unless the context specifically indicates the contrary.

I claim:

1. A method for treating or reducing susceptibility to a microbial infection in the lower genital tract of a female mammal comprising infusing into the lower genital tract of the mammal an effective amount of an aqueous composition comprising greater than about 125 ppm to about 1000 ppm chlorine dioxide and a pharmaceutically acceptable carrier, wherein the molar ratio of chlorine dioxide to chlorite in the composition is at least 5:1 and the pH is compatible with the tract.

2. A method according to claim 1 wherein the composition contains from greater than about 125 ppm to about 600 ppm chlorine dioxide.

3. A method according to claim 1 wherein the mammal is post-parturient.

4. A method according to claim 1 wherein the chlorine dioxide in the composition is produced by the reaction of a chlorine dioxide generating compound and an acid.

5. A method according to claim 4 wherein the chlorine dioxide generating compound is a water-soluble chlorite selected from the group consisting of an alkali metal chlorite, an alkaline earth metal chlorite, and mixtures thereof.

6. A method according to claim 5 wherein the chlorine dioxide in the composition is produced by a process selected from the group consisting of:

(a) reaction of a chlorite with a mineral acid and adjustment of the pH to about 5 to about 7.5;

(b) reaction of a chlorite with an organic acid having a pK of from about 2.8 to about 4.2; and (c) reaction of a chlorite with a saccharide, which has been heat-activated by heating the saccharide to a temperature of from about 50° C. to about 150° C. for at least about 1 minute, in a solution in the presence of an organic acid having a pK of from about 2.8 to about 4.2 and a pH below about 5.5.

7. A method according to claim 6 wherein the saccharide is selected from the group consisting of glucose, galactose, mannose, ribose, rhamnose, lactose, sucrose, maltose, and mixtures thereof.

8. A method according to claim 5 wherein the chlorite is sodium chlorite.

9. A method according to claim 1 wherein the mammalian female lower genital tract microbial infection is selected from the group consisting of vulvitis, vaginitis, cervicitis, endometritis and mixtures thereof.

10. A method according to claim 9 wherein the infection is equine endometritis.

11. A method according to claim 9 wherein the infection is caused by an organism selected from the group consisting of Candida, Trichomonas, Corynebacterium, Campylobacter, Pseudomonas, Streptococcus, Klebsiella, and Escherichia species.

12. A method according to claim 9 wherein the chlorine dioxide in the composition is produced by reaction of an acid with a water-soluble chlorite selected from the group consisting of alkali metal chlorites, alkaline earth metal chlorites, and mixtures thereof.

13. A method according to claim 12 wherein the composition is adjusted to a pH of about 5 to about 7.5 after the reaction.

14. A method according to claim 12 wherein the acid is a mineral acid selected from the group consisting of sulfuric acid, hydrochloric acid, and phosphoric acid.

15. A method according to claim 12 wherein the acid is an organic acid selected from the group consisting of citric acid, malic acid, lactic acid, mandelic acid, tartaric acid, and mixtures thereof.

16. A method according to claim 15 wherein the composition further comprises an isotonic solution of chloride salts.

17. A method according to claim 16 wherein the reaction is carried out in the presence of a heat-activated saccharide compound prepared by heating a saccharide selected from the group consisting of glucose, galactose, mannose, ribose, rhamnose, lactose, sucrose, maltose, and mixtures thereof, to a temperature of from about 50° C. to about 150° C. for at least about 1 minute.

18. A method according to claim 5 wherein the chlorite is sodium chlorite and the composition has a pH of about 5 to about 7.5.

19. A method for treating or reducing susceptibility to post-parturient microbial infections in the lower genital tract of mares or cows comprising infusing into the tract of the cow or mare after birth 1 to 5 liters of a solution that contains a chlorite selected from the group consisting of an alkali metal chlorite, an alkaline earth metal chlorite, and mixtures thereof, reacted with an acid in amounts sufficient to yield greater than about 125 ppm to about 1000 ppm chlorine dioxide, provided that the ratio of chlorine dioxide to chlorite in the solution is at least 5:1, and the pH of the composition is compatible with the tract.

20. A method according to claim 19 wherein the chlorite is sodium chlorite and the composition has a pH of about 5 to about 7.5.

* * * * *